(12) United States Patent
Herman

(10) Patent No.: US 7,821,778 B2
(45) Date of Patent: Oct. 26, 2010

(54) MONITOR ASSEMBLY FOR DIAGNOSTIC DEVICE

(76) Inventor: Kevin Herman, 73 John Pl., Bergenfield, NJ (US) 07621

( * ) Notice: Subject to any disclaimer, the term of this patent is extended or adjusted under 35 U.S.C. 154(b) by 413 days.

(21) Appl. No.: 11/953,948

(22) Filed: Dec. 11, 2007

(65) Prior Publication Data

US 2008/0139917 A1    Jun. 12, 2008

Related U.S. Application Data

(60) Provisional application No. 60/874,099, filed on Dec. 12, 2006.

(51) Int. Cl.
*H05K 5/00* (2006.01)
*H05K 7/00* (2006.01)
*H05G 1/64* (2006.01)
*H05G 1/02* (2006.01)
*G21K 4/00* (2006.01)

(52) U.S. Cl. ............................ 361/679.01; 361/679.06; 361/679.07; 378/98; 378/190; 378/193

(58) Field of Classification Search ............ 361/679.04, 361/679.06, 679.07, 679.27, 679.01; 378/98, 378/190, 208, 195, 193
See application file for complete search history.

(56) References Cited

U.S. PATENT DOCUMENTS

| | | | |
|---|---|---|---|
| 6,256,374 B1 * | 7/2001 | Tomasetti et al. | 378/98.2 |
| 6,363,134 B1 * | 3/2002 | Suzuki | 378/15 |
| 2005/0146845 A1 * | 7/2005 | Moscovitch | 361/681 |

* cited by examiner

*Primary Examiner*—Jayprakash N Gandhi
*Assistant Examiner*—Anthony M Haughton

(57) ABSTRACT

A monitor assembly includes a monitor, for displaying output of a diagnostic device such as a fluoroscope, to which is operationally attached a bracket that is operative to secure (preferably reversibly) the monitor to the diagnostic device so that an operator of the diagnostic device can view the output while operating the diagnostic device and without interrupting the operation of the diagnostic device. Preferably, the monitor is attached to the bracket by a joint assembly that allows the monitor to be translated and rotated relative to the bracket.

8 Claims, 6 Drawing Sheets

MONITOR ASSEMBLY FOR DIAGNOSTIC DEVICE

This is a continuation-in-part of U.S. Provisional Patent Application No. 60/874,099, filed Dec. 12, 2006

FIELD AND BACKGROUND OF THE INVENTION

The present invention relates generally to medical diagnostic equipment and, more particularly, to a monitor assembly for a diagnostic device such as a fluoroscope. The primary function of fluoroscopy is to provide real-time imaging and visualization of dynamic processes as they occur. For example, a fluoroscope is used to determine a diagnosis or provide treatment from a live, real-time display of patient anatomy. During a fluoroscopic examination, the operator controls activation of the x-ray tube for real-time imaging of the patient. Generally, the patient's physician who performs the examination operates the fluoroscopic equipment.

A closed-circuit television system is used to view the image. The television system allows for real-time viewing of the fluoroscopic image by several people at once on one monitor or on multiple monitors.

In conventional systems, the monitor or monitors are mounted either on a movable cart or on a bracket hanging from the ceiling of the fluoroscopy suite. There are several problems that a fluoroscopist or angiographer faces when using such configurations.

Inconvenience. It is inconvenient for the fluoroscopist to view images at a distance. Furthermore, conventional configurations create an awkward viewing angle while operating the fluoroscopic equipment.

Physician Safety. When the fluoroscopist turns his/her body to view the examination in real-time he/she puts him/herself at a risk for increased radiation exposure. In fact, while the operator's body faces forward his/her head must be turned/angled to view the monitor. This places undue strain on the operator's upper body and neck, possibly resulting in premature degenerative disease.

Patient safety. When the fluoroscopist turns his/her body to view the examination he/she no longer faces the patient who is undergoing the examination, thereby placing the patient at risk.

General Safety. The movable cart setup utilizes bulky carts containing large electrical cords. This poses a risk as a stumbling block for all personnel in the fluoroscopy suite. Furthermore, many examinations performed in the fluoroscopy suite, in the interventional radiology suite or in the cardiac catheterization laboratory take place in conjunction with bulky equipment such as large anesthesia carts and endoscopic tools. Less clutter would be a logistical improvement.

Accordingly it would be advantageous to provide a mechanical solution to the abovementioned problems leading to enhanced ergonomic access to the fluoroscope with secure positioning and mobility of the monitor assembly. The potential improvements gained from the present design will effectively result in enhanced performance of the radiologist as well as increased patient and physician safety.

SUMMARY OF THE INVENTION

According to the present invention there is provided a monitor assembly including: a monitor for displaying output of a diagnostic device; and a bracket, operationally attached to the monitor, and operative to secure the monitor to the diagnostic device in a manner that enables an operator of the diagnostic device to see the output while operating the diagnostic device and without interrupting the operation of the diagnostic device.

According to an aspect of the present invention there is provided a method of performing a medical procedure. The method includes: providing a monitor assembly that includes a monitor for displaying output of a diagnostic device, and a bracket, operationally attached to the monitor, and operative to secure the monitor to the diagnostic device in a manner that enables an operator of the diagnostic device to view the output while operating the diagnostic device and without interrupting the operation of the diagnostic device; securing the monitor assembly to the diagnostic device in the manner; and operating the diagnostic device while looking at the output on the monitor.

An aspect of the present invention provides a monitor assembly including a monitor and a bracket. The monitor is for displaying the output of a diagnostic device. The bracket is operationally attached to the monitor, for (preferably reversibly) reversibly securing the monitor to the diagnostic device in a way that enables an operator of the diagnostic device to see the output on the monitor while operating the diagnostic device and without having to turn to look at a monitor that is mounted or deployed separately from the diagnostic device.

In an aspect of the invention the monitor assembly also includes a joint assembly for operationally attaching the monitor to the bracket in a manner that allows the monitor to be moved (e.g. translated or rotated) relative to the bracket. For example, a preferred embodiment of the monitor assembly, the joint assembly includes a ball joint for rotational movement and/or a tilt hinge for both rotational movement and translational movement.

The diagnostic device may be a fluoroscope. The bracket may be adapted to be rigidly attached to e.g. the image intensifier tower and housing of the fluoroscope, the flat detector of the fluoroscope or the C-arm of the fluoroscope.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and accompanying drawings in which:

FIGS. 1A and 1B are perspective views and FIG. 1C is a side view;

FIG. 2A is a perspective view and FIG. 2B is a side view;

FIG. 4A is a top view of the monitor assembly, FIG. 4B is a perspective view of the monitor assembly, and FIG. 4C is a side view of the monitor assembly;

DESCRIPTION OF THE PREFERRED EMBODIMENTS

The principles and operation of a monitor assembly according to the present invention may be better understood with reference to the figures, wherein like reference numbers identify like elements throughout the various figures, and the accompanying description.

Figure 1A:
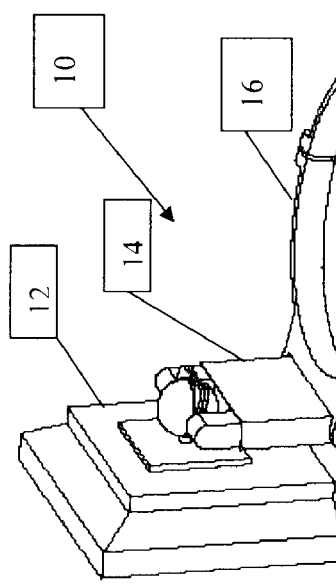
FIGS. 1A-1C illustrate a first embodiment of a monitor assembly.
Figure 1B:
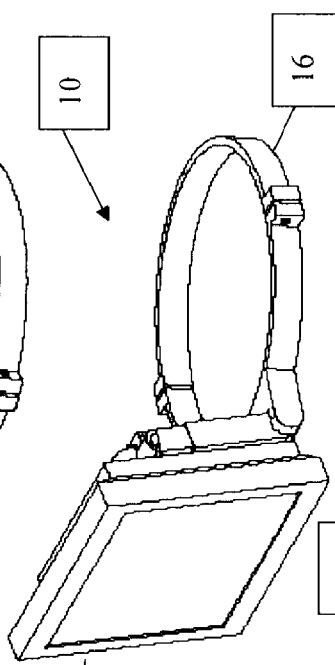
Figure 1C:
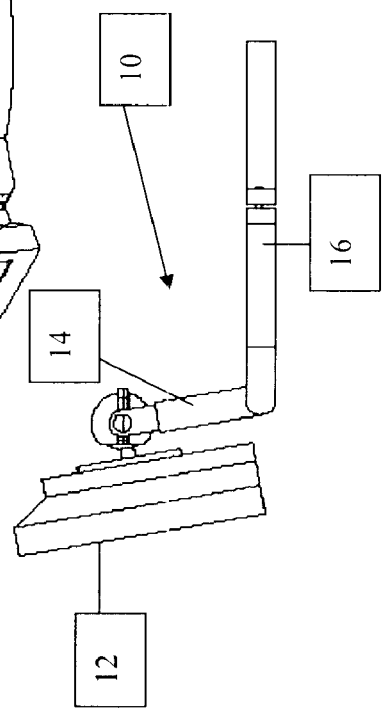
Figure 2A:
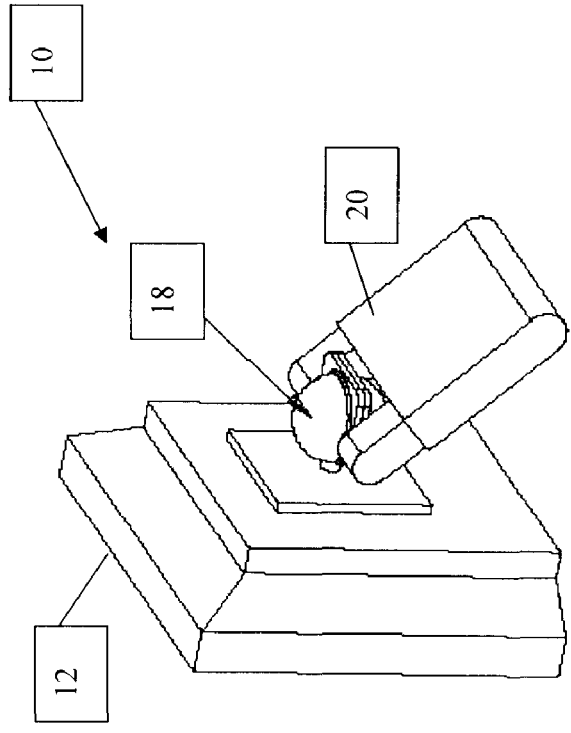
FIGS. 2A and 2B show details of the joint assembly of the first monitor assembly.
Figure 2B:
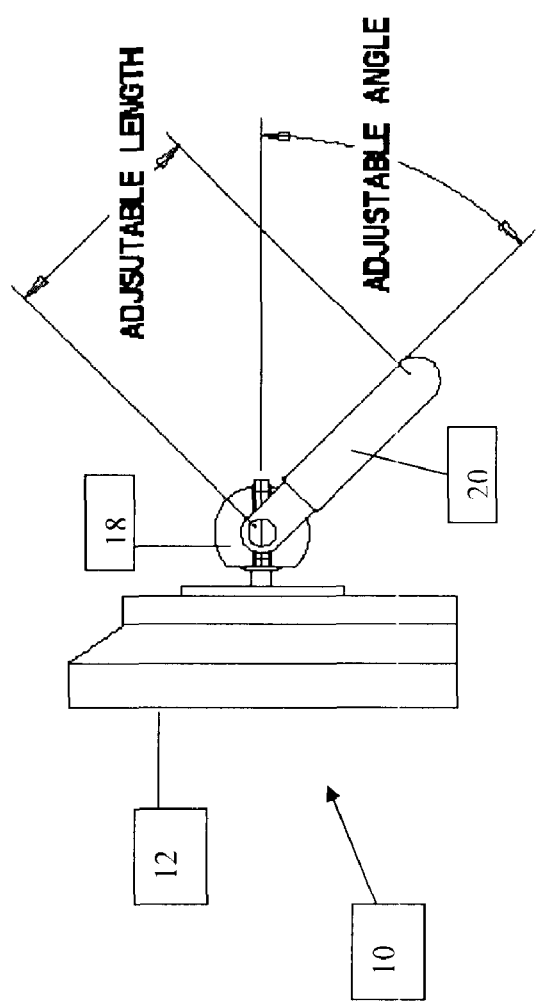

Referring now to the drawings, FIGS. 1A through 1C illustrate an embodiment 10, of a monitor assembly of the present invention, that is intended to be used with a General Electric Precision 500D Radiography Fluoroscopy Unit (General Electric Company, Fairfield, Conn., USA). While a General Electric Precision 500D Radiography Fluoroscopy Unit is preferred, those skilled in the art will recognize that the invention is not limited to this brand of fluoroscope or to any fluoroscope. The invention may be employed, either as illustrated or with slight modifications, with other brands of fluoroscopes and other equipment without departing from the spirit and scope of the invention. Monitor assembly 10 includes a conventional monitor 12 such as a FIMI-Philips LCD MML 1821 series monitor (FIMI Philips, Saronno, Italy) or some other appropriate monitor, a joint assembly 14 and a bracket 16. FIGS. 2A and 2B show details of joint assembly 14. Joint assembly 14 includes a ball joint 18 and an adjustable arm 20. Monitor 12 is rigidly attached to ball joint 18. Both the length of arm 20 and the angle between arm 20 and ball joint 18 are adjustable, as shown. The end of arm 20 is rigidly attached to bracket 16, as shown in FIGS. 1A-1C. Ball joint 18 allows monitor 12 to be swiveled relative to arm 20, and arm 20 allows monitor 12 and ball joint 18 to be moved together up and down (angular adjustment) and in and out (length adjustment) relative to bracket 16 and hence relative to the fluoroscopy unit to which monitor assembly 10 is secured. Joint assembly 14 and bracket 16 are made of a suitably rigid material. Examples of some suitable materials include metals such as aluminum and polymers such as acrylonitrile butadiene styrene and polycarbonate.

Figure 3:
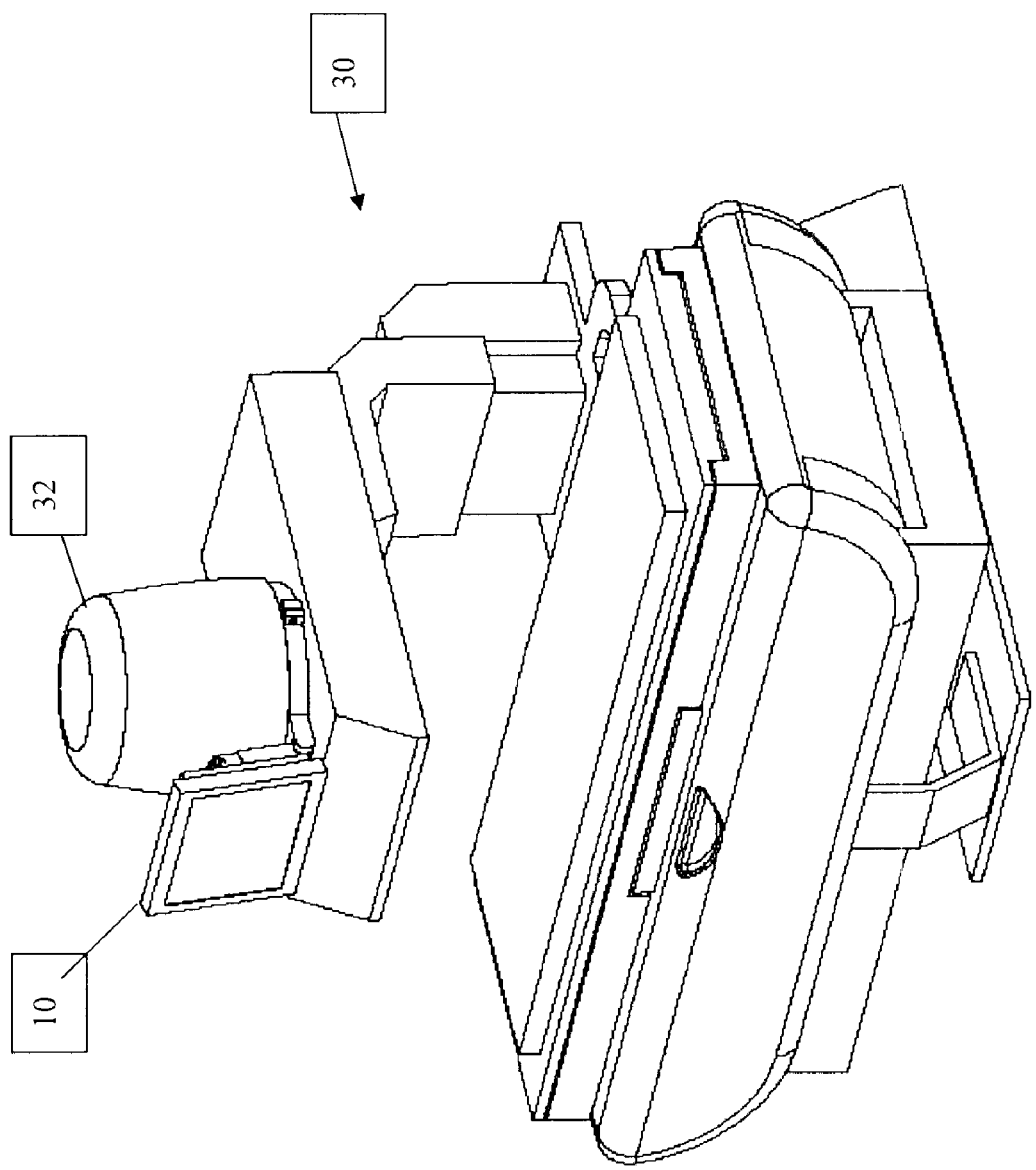
FIG. 3 shows the first monitor assembly secured to a GE image intensifier tower and housing.

FIG. 3 shows monitor assembly 10 reversibly secured to the image intensifier/housing 32 of a General Electric Radiography Fluoroscopy Unit 30. A fluoroscopist can easily adjust the orientation of monitor 12 and (within the limits of translational extension of arm 14) the distance between monitor 12 and image intensifier tower 32. A fluoroscopist also can position a patient as desired on the examination table of the Fluoroscopy Unit 30 and conduct diagnostic procedures while looking at the display of the imaging output from Fluoroscopy Unit 30 on monitor 12 without turning his or her body away from Fluoroscopy Unit 30 and without interrupting the diagnostic procedures. The examination table can be placed at any angle relative to the floor, from horizontal to vertical; and monitor assembly 10 can be adjusted accordingly for the convenience of the fluoroscopist. Additional monitors may be provided in the conventional manner so that personnel other than the fluoroscopist can see the same display that the fluoroscopist sees.

Figure 4:
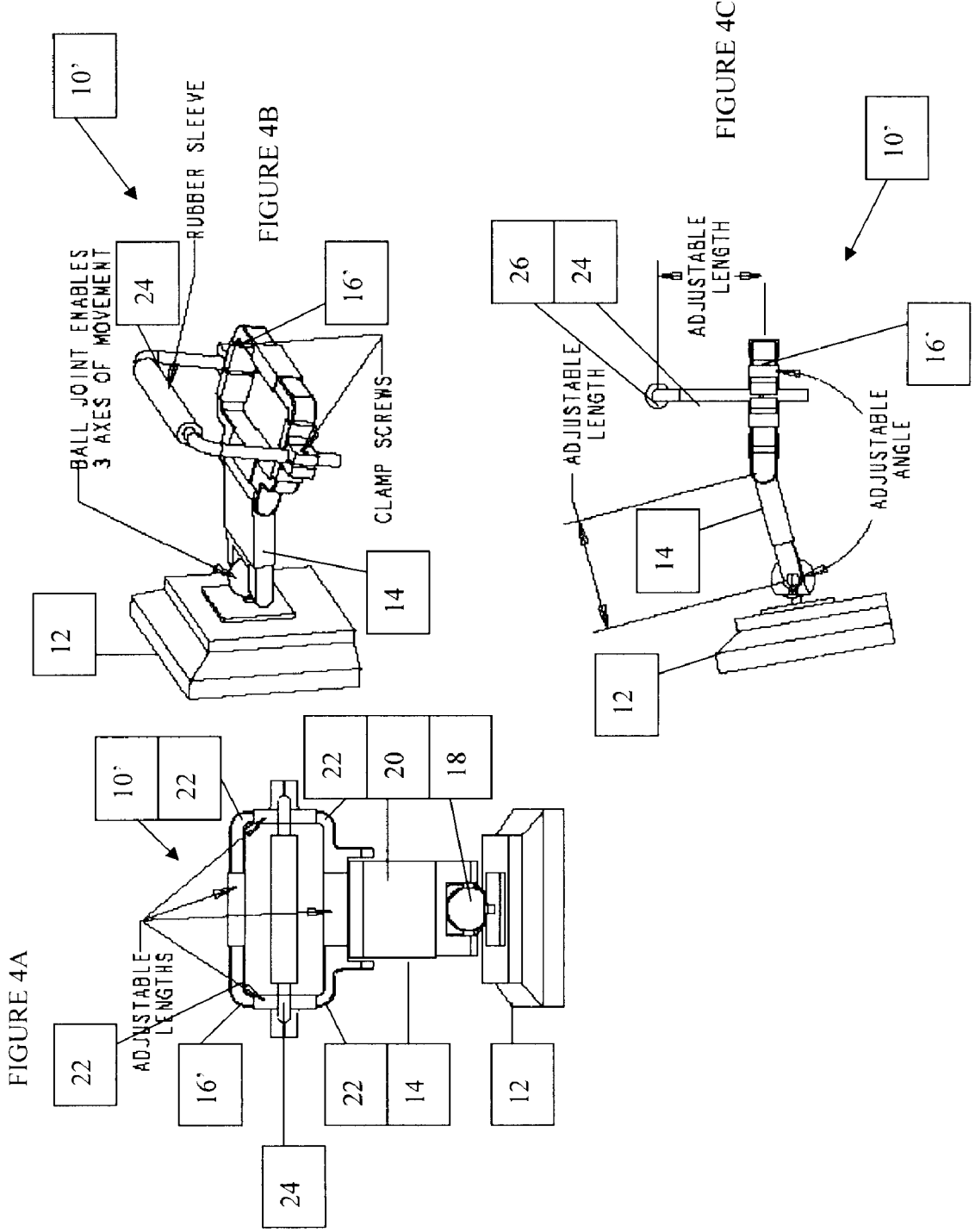
FIGS. 4A-4C illustrate a second embodiment of a monitor assembly.
Figure 5:
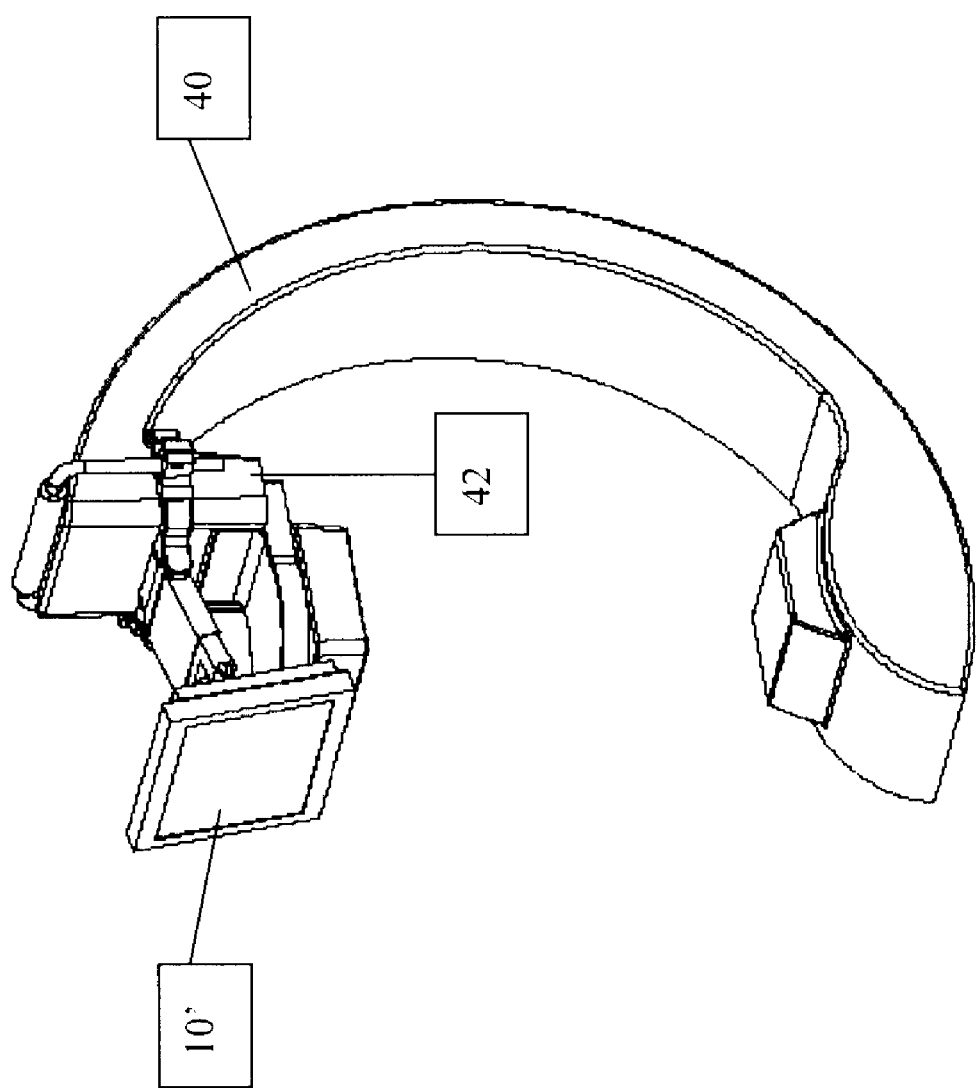
FIG. 5 shows the second monitor assembly secured to a Phillips C-arm flat detector.

FIGS. 4A-4C illustrate another embodiment 10', of a monitor assembly of the present invention, that is intended to be used with a Phillips Allura Xper Fluoroscopy Unit (Koninklijke Philips Electronics N.V., Eindhoven, The Netherlands). Monitor assembly 10' may employ the same monitor 12 and joint assembly 14 as monitor assembly 10 but a different bracket 16'. Bracket 16' includes four L-pieces 22 arranged in a rectangular shape of adjustable length and width, as shown in FIG. 4A, and also an orthogonal brace 24 that is secured to the L-piece arrangement by clamp screws, as shown in FIG. 4B, so as to allow the separation of the distal end 26 of orthogonal brace 24 from the L-piece arrangement to be adjusted, as shown in FIG. 4C. While four L-shaped pieces and adjustability of both the length and width are preferred, those skilled in the art will recognize that different shapes could be employed to achieve the same adjustability and shape and the L-piece arrangement could have a fixed length and/or width and still fall within the scope of the invention. Those skilled in the art will also recognize that orthogonal brace 24 could be fixedly secured to the L-piece arrangement and the L-Piece arrangement could be separable to achieve the same or similar results and still fall within the scope of the invention. FIG. 5 shows monitor assembly 10' reversibly secured to the flat detector 42 of the C-arm 40 of a Phillips Allura Xper Fluoroscopy Unit. Orthogonal brace 24 is shown cushioned against the top of flat panel detector by a rubber sleeve, although it need not be to fall within the scope of the invention.

Figure 6B:
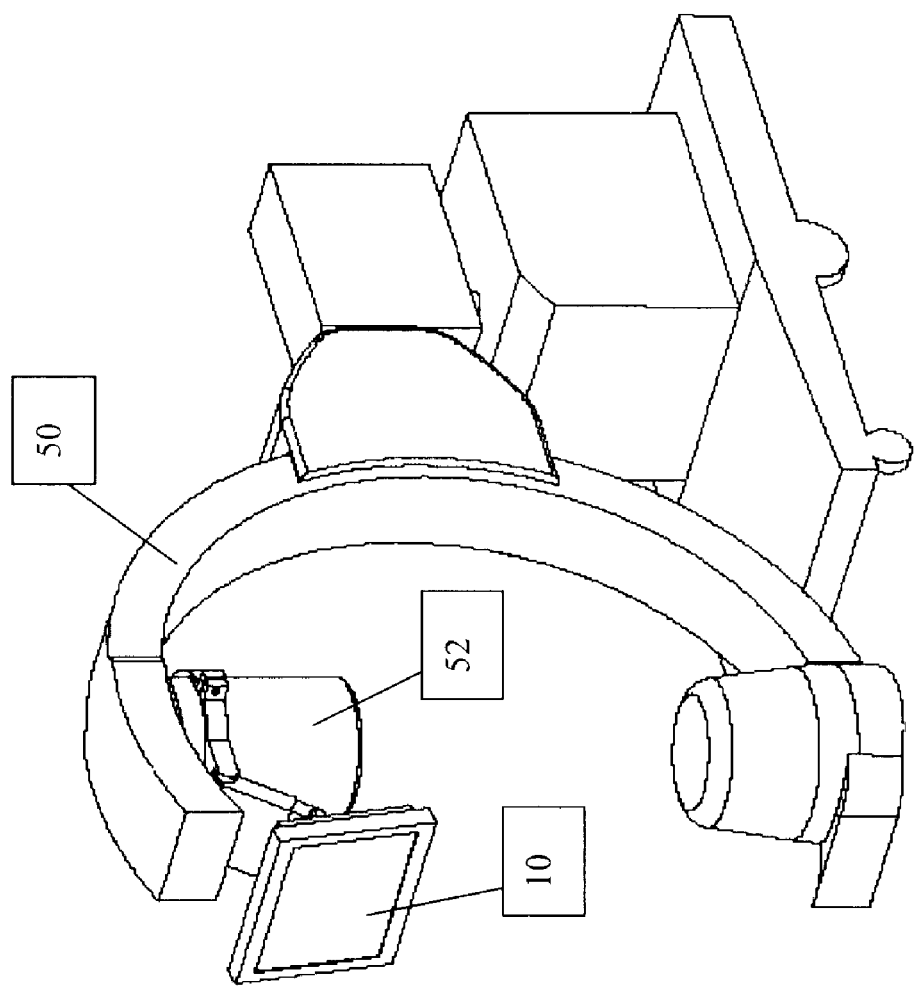
FIGS. 6A and 6B show the first monitor assembly secured to a Siemens SIREMOBILE C-arm.
Figure 6A:
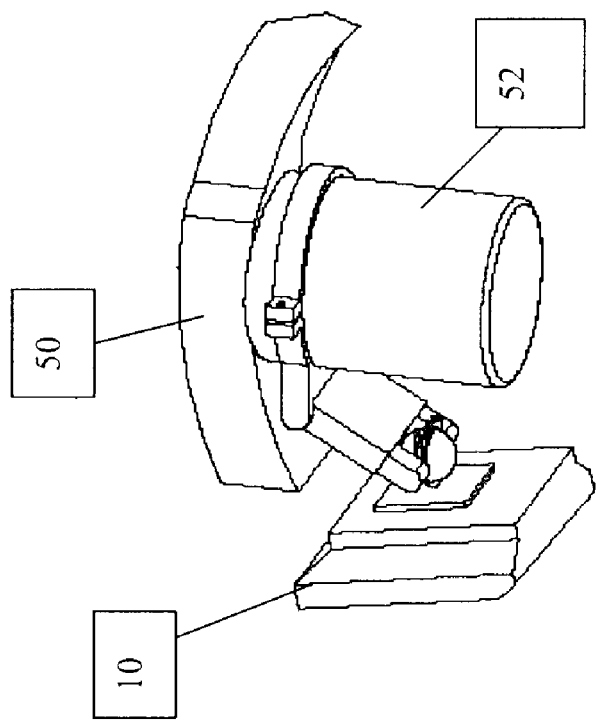

In general, the bracket of a monitor assembly of the present invention may be either custom-designed for a specific type of diagnostic device, or semi-custom-designed for a class of diagnostic devices of similar geometry, or a universal bracket that is adaptable to a wide range of diagnostic devices. The illustrated brackets 16 and 16' are of the second type: brackets that are designed for a class of diagnostic devices of similar geometry. For example, FIGS. 6A and 6B are two views of monitor assembly 10 with bracket 16 reversibly secured to the image intensifier tower 52 of the ISO-C-arm 50 of a Siemens SIREMOBILE Unit (Siemens AG, Berlin and Munich, Germany).

While the invention has been described with respect to a limited number of embodiments, it will be appreciated that many variations, modifications and other applications of the invention may be made. For example, the connection to the monitor need not be a ball joint. It could be a fixed connection, a connection that only has movement in one direction, or in 2 directions rather than a free range of directions. Such connections are conventional and need not be described further. Further, the arm could be a fixed length, telescoping or of an accordion type. These various arms are also well known and thus need not be described further. Those skilled in the art will recognize that additional joints could be employed to further enhance the degree of movement of the monitor relative to the diagnostic device.

It is to be understood that the following claims are intended to cover all of the generic and specific features of the invention as described herein, and all statements of the scope of the invention, which as a matter of language, might be said to fall therebetween.

What is claimed is:

1. A monitor assembly comprising:
   a monitor configured to display output from a diagnostic device; wherein the monitor has a
   front portion which displays output, and a rear portion that has a connecting member and
   a bracket, which has a front portion operationally attached to said monitor, and a rear portion
   operative to secure said monitor to said diagnostic device in a manner that enables an operator of said diagnostic device to see said output while operating said diagnostic device and
   without interrupting said operation of said diagnostic device wherein said diagnostic device is a fluoroscope having an image intensifier and housing, a flat detector and a C-arm.

2. The monitor assembly of claim 1, wherein said bracket is operative to secure said monitor reversibly to said diagnostic device.

3. The monitor assembly of claim 1, wherein said operational attachment includes:
   a joint assembly for attaching said monitor to said bracket in a manner that allows said monitor to be moved relative to said bracket.

4. The monitor assembly of claim 3, wherein said movement includes translational movement.

5. The monitor assembly of claim 3, wherein said movement includes rotational movement.

6. The monitor assembly of claim 3, wherein said joint assembly includes a ball joint.

7. The monitor assembly of claim 3, wherein said joint assembly includes a tilt hinge.

8. The monitor assembly of claim 1, wherein said bracket is adapted to be rigidly attached to a component of said fluoroscope selected from the group consisting of the image intensifier and housing, the flat detector and the C-arm.

* * * * *